(12) United States Patent
Lee et al.

(10) Patent No.: US 10,568,584 B2
(45) Date of Patent: Feb. 25, 2020

(54) APPARATUS FOR ESTIMATING BLOOD COMPONENT LEVEL USING SPECTRUM ANALYSIS

(71) Applicant: SAMSUNG ELECTRONICS CO., LTD., Suwon-si (KR)

(72) Inventors: Joon Hyung Lee, Yongin-si (KR); So Young Lee, Daejeon (KR); Sang Kyu Kim, Yongin-si (KR); Jung Yong Nam, Hwaseong-si (KR); Jung Mok Bae, Seoul (KR); Ki Young Chang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 779 days.

(21) Appl. No.: 15/221,757

(22) Filed: Jul. 28, 2016

(65) Prior Publication Data

US 2017/0150931 A1 Jun. 1, 2017

(30) Foreign Application Priority Data

Nov. 30, 2015 (KR) .................... 10-2015-0168970

(51) Int. Cl.
*A61B 5/00* (2006.01)
*A61B 5/1455* (2006.01)
*A61B 5/145* (2006.01)

(52) U.S. Cl.
CPC .......... *A61B 5/7282* (2013.01); *A61B 5/1455* (2013.01); *A61B 5/14532* (2013.01); *A61B 5/14546* (2013.01); *A61B 5/0075* (2013.01)

(58) Field of Classification Search
CPC .............. A61B 5/7282; A61B 5/14532; A61B 5/14546; A61B 5/1455; A61B 5/0075
See application file for complete search history.

(56) References Cited

U.S. PATENT DOCUMENTS

| 5,610,836 A * | 3/1997 | Alsmeyer ............ G01N 21/274 |
| | | 702/27 |
| 5,729,333 A * | 3/1998 | Osten ................. A61B 5/14535 |
| | | 356/39 |

(Continued)

FOREIGN PATENT DOCUMENTS

| JP | 2004-226277 A | 8/2004 |
| JP | 2010-43942 A | 2/2010 |
| WO | 2007/071092 A1 | 6/2007 |

OTHER PUBLICATIONS

Munsters et al., "Effects of Meal Frequency on Metabolic Profiles and Substrate Partition on Lean Healthy Males", Plos One, vol. 7, Iss. 6, pp. 1-8, Jun. 2012 (Year: 2012).*

(Continued)

*Primary Examiner* — Eric F Winakur
*Assistant Examiner* — Abid A Mustansir
(74) *Attorney, Agent, or Firm* — Sughrue Mion, PLLC

(57) ABSTRACT

An apparatus for estimating a blood component level, such as a blood neutral fat level or blood sugar level, is provided. The apparatus may include: a light source configured to emit a light toward a skin; a spectrometer configured to spectrally disperse the light reflected from the skin; a detector configured to detect a spectrum of the spectrally dispersed light to extract spectrum data for each wavelength; and a controller configured to apply the extracted spectrum data and a reference blood component level corresponding to the spectrum data to a first level estimation model to estimate a target blood component level.

14 Claims, 6 Drawing Sheets

(56) References Cited

U.S. PATENT DOCUMENTS

| | | | | |
|---|---|---|---|---|
| 6,280,381 B1* | 8/2001 | Malin | ................ | A61B 5/14532 |
| | | | | 128/920 |
| 7,460,895 B2 | 12/2008 | Arnold et al. | | |
| 9,057,689 B2 | 6/2015 | Soiler et al. | | |
| 2003/0109998 A1* | 6/2003 | Lorenz | ............... | A61B 5/14532 |
| | | | | 702/85 |
| 2007/0043518 A1* | 2/2007 | Nicholson | ............. | G06F 19/703 |
| | | | | 702/23 |
| 2012/0035442 A1* | 2/2012 | Barman | ............. | A61B 5/14532 |
| | | | | 600/316 |

OTHER PUBLICATIONS

Shengtian Pan et al., "Near-Infrared Spectroscopic Measurement of Physiological Glucose Levels in Variable Matrices of Protein and Triglycerides", Analytical Chemistry, American Chemical Society, vol. 68, No. 7, 1996 pp. 1124-1135.

* cited by examiner

FIG. 2

$$Y_T = F(w_1, w_2, \ldots, w_n, y_R)$$
$$= \underbrace{f_1(w_1, w_2, \ldots, w_n)}_{\text{WAVELENGTH FUNCTION}} + \underbrace{f_2(y_R)}_{\text{REFERENCE FUNCTION}}$$

FIG. 3

$Y'_{T1} = F(w_{11}, w_{21}, \ldots, w_{n1}, y'_{R1})$  at  t=t1
$Y'_{T2} = F(w_{12}, w_{22}, \ldots, w_{n2}, y'_{R2})$  at  t=t2
$\vdots$
$Y_{Tm} = F(w_{1m}, w_{2m}, \ldots, w_{nm}, y'_{Rm})$  at  t=tm

APPARATUS FOR ESTIMATING BLOOD COMPONENT LEVEL USING SPECTRUM ANALYSIS

CROSS-REFERENCE TO RELATED APPLICATION

This application claims priority from Korean Patent Application No. 10-2015-0168970, filed on Nov. 30, 2015 in the Korean Intellectual Property Office, the disclosure of which is incorporated herein by reference in its entirety.

BACKGROUND

1. Field

Apparatuses and methods consistent with exemplary embodiments relate to estimating a specific component level included in blood, such as a blood sugar level, a neutral fat level, or the like, using spectrum analysis.

2. Description of Related Art

An optical measurement method using infrared rays or near infrared rays (NIR) is known as one of methods for estimating a specific component level included in blood such as a blood sugar level or neutral fat level. When the optical measurement method is used, a level of a specific component measured from a human subject may be estimated in a non-invasion manner. As an example of such an optical measurement method, there is spectrum analysis which detects a specific component and/or measures a concentration thereof using a spectrum of reflected light.

The spectrum analysis uses the principle that a spectrum of reflected light is changed according to a type and/or concentration of a specific material included in blood. To this end, the spectrum analysis is performed by using a spectrometer that spectrally disperses light (e.g., NIR) reflected off the skin of the human subject emitted. Further, a spectrum of the reflected light spectrally dispersed by the spectrometer is applied to a concentration estimation model of a predetermined preset blood component so that a concentration of a specific material included in blood can be estimated.

According to a spectrum analysis method in the related art, only spectrum data of reflected light may be used for estimating the concentration of a blood component. Accordingly, a concentration estimation model of a blood component is defined by a function of wavelengths forming the spectrum, and spectrum data for each wavelength are applied to a concentration estimation model to be used for estimating the blood component. Therefore, measurement information using an optical measurement apparatus, such as an NIR spectrometer, is a spectrum of the reflected light, that is, spectrum data for each wavelength.

Such a spectrum analysis method in the related art is performed based on the assumption that an actual measurement process is always constantly performed and is accurately performed as much as possible. However, even though the measurement is performed by a skilled person using a special medical device, the measured result can be changed according to a measurement situation or a surrounding environment, and an accurate measurement cannot be performed in some cases.

In addition, when an unskilled person uses an optical measurement module mounted on a portable electronic device (e.g., smart phone) or a wearable electronic device (e.g., a smart band, a smart watch, or smart glasses) to perform the measurement, it may be more difficult to obtain a constant and accurate measurement.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide an apparatus for estimating a blood component level using a spectrum analysis method capable of more accurately estimating the blood component level.

Further, one or more exemplary embodiments provide an apparatus for estimating a blood component level using a spectrum analysis method capable of improving accuracy of measurement and estimation even when a measurement situation, a surrounding environment, an operation of a user, or the like is variable.

Still further, one or more exemplary embodiments provide an apparatus for estimating a blood component level using a spectrum analysis method capable of continuously measuring a concentration of neutral fat.

According to an aspect of an exemplary embodiment, there is provided an apparatus for estimating a blood component level including: a light source configured to emit a light toward a skin; a spectrometer configured to spectrally disperse the light reflected from the skin; a detector configured to detect a spectrum of the spectrally dispersed light to extract spectrum data for each wavelength; and a controller configured to apply the extracted spectrum data and a reference blood component level corresponding to the spectrum data to a first level estimation model to estimate a target blood component level.

According to an aspect of another exemplary embodiment, there is provided an apparatus for estimating a blood neutral fat level including: a light source configured to emit a light toward a skin; a spectrometer configured to spectrally disperse the light reflected from the skin; a detector configured to detect a spectrum of the spectrally dispersed light to extract spectrum data for each wavelength; and a controller configured to apply the extracted spectrum data and a blood sugar level corresponding to the spectrum data to a blood neutral fat level estimation model to estimate a blood neutral fat level.

According to another aspect of an exemplary embodiment, there is provided an apparatus for estimating a blood sugar level including: a light source configured to emit a light toward a skin; a spectrometer configured to spectrally disperse the light reflected from the skin; a detector configured to detect a spectrum of the spectrally reflected light to extract spectrum data for each wavelength; and a controller configured to apply the extracted spectrum data and a blood neutral fat level corresponding to the spectrum data to a first level estimation model to estimate the blood sugar level.

BRIEF DESCRIPTION OF THE DRAWINGS

The above and/or other aspects will be more apparent by describing certain exemplary embodiments, with reference to the accompanying drawings, in which:

FIG. 2 is an example of a level estimation model conceptually expressed by using an equation.

FIG. 3 shows equations for describing a process of deriving a combination function F using a measured value of a spectrum for each wavelength, a measured value of a target blood component, and a measured value of a reference blood component.

DETAILED DESCRIPTION

Figure 1:
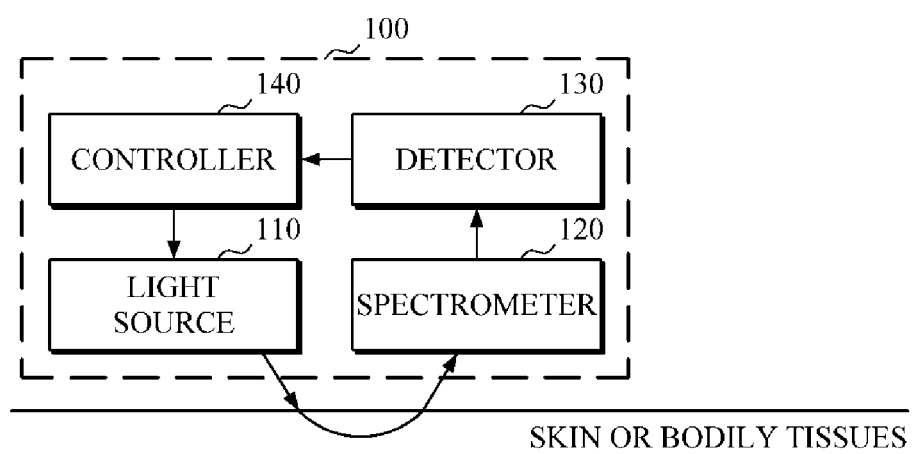
FIG. 1 is a block diagram illustrating a configuration of an apparatus for estimating a blood component level using a spectrum analysis method according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

FIG. 1 is a block diagram illustrating a configuration of an apparatus for estimating a blood component level using a spectrum analysis method according to an exemplary embodiment. Referring to FIG. 1, an apparatus for estimating a blood component level 100 includes a light source 110, a spectrometer 120, a detector 130, and a controller 140.

The light source 110 emits light according to a control signal. The control signal is generated by a control unit which controls an operation of the apparatus for estimating a blood component level 100 and may be transmitted to the light source 110. The control unit is implemented for one function of the controller 140 to be described below, but is not limited thereto. The light source 110 emits light having a predetermined wavelength, for example, near infrared rays (NIR), for measurement according to the control signal. However, a wavelength of the light emitted from the light source 110 may be changed according to a purpose of measurement or a type of a component to be measured. Further, the light source 110 may be implemented with a single illuminant, or a group of a plurality of illuminants. In the latter case, the plurality of illuminants may emit light having wavelengths different from each other for the purpose of measurement or may emit light having the same wavelength.

The light source 110 emits measurement light in a predetermined direction for measurement. A direction of the measurement light emitted from the light source 110 may be permanently fixed or changeable. For the latter case, the apparatus for estimating a blood component level 100 may include a unit for changing an incident direction of the light of the light source 110 or an additional light path change unit for changing a path of the light emitted from the light source 110. Such a light path change unit may be integrated with the light source 110 or separated a predetermined distance from light source 110.

The measurement light emitted from the light source 110 is reflected from a predetermined object to be measured, for example, skin, and the reflected light is spectrally dispersed by the spectrometer 120. That is, the spectrometer 120 receives the reflected light from skin and decomposes the reflected light according to a wavelength difference. The reflected light received by the spectrometer 120 may be evanescent waves or simple reflected waves reflected from the skin or bodily tissues, and may be changed according to a type, an operation principle, or the like of the apparatus for estimating a blood component level 100. In the former case, the apparatus for estimating a blood component level 100 may be an apparatus using attenuated total reflectance (ATR), and in the latter case, the apparatus for estimating a blood component level 100 may be an apparatus using simple reflected waves.

The detector 130 detects a spectrum of the reflected light that is spectrally dispersed by the spectrometer 120 to extract spectrum data for each wavelength. For example, the detector 130 may extract intensity for each spectrum wavelength from an intensity spectrum of the reflected light decomposed by the spectrometer 120 on the basis of a wavelength difference. In this case, the spectrum data for each wavelength becomes intensity of the reflected light for each wavelength. However, the spectrum data for each wavelength is not limited thereto, and may be each a measured value for other wavelengths currently used or to be used in the future in related fields.

The controller 140 estimates or determines a level of a predetermined component included in blood, that is, a blood component (hereinafter, referred to as a 'target blood component'), using the spectrum data for each wavelength extracted by the spectrometer 120. Here, the controller 140 may the extracted spectrum data for each wavelength, and may also use a level of another type of a blood component (hereinafter, referred to as a 'reference blood component') different from the target blood component. For example, when the target blood component is neutral fat present in the blood, the controller 140 may use the spectrum data for each wavelength extracted by the detector 130, and may also use a level of blood sugar or another type of a blood component as a reference blood component. Further, when the target blood component is blood sugar, the controller 140 may use the spectrum data for each wavelength extracted by the detector 130 together with a level of blood neutral fat or another type of a blood component as the reference blood component.

In this case, the reference blood component level may be an estimated value implemented by using the spectrum data for each wavelength extracted by the detector 130. To this end, the controller 140 may estimate or determine a level according to a predetermined algorithm using the spectrum data for each wavelength extracted by the detector 130 or may estimate the level by applying the spectrum data for each wavelength extracted by the detector 130 to a level estimation model with respect to the reference blood component.

In the algorithm used in the controller 140 for obtaining the target blood component level or the level estimation model with respect to the reference blood component, the spectrum data for each wavelength may be used as an input parameter. That is, the reference blood component level may be estimated by using the spectrum data for each wavelength. This may be different from using the spectrum data for each wavelength together with the reference blood component level as an additional input parameter when the controller 140 may estimate the target blood component level. However, the exemplary embodiment is not limited thereto. A third blood component level as an input parameter of the level estimation model rather than the target blood component or the reference blood component may be used together with the spectrum data for each wavelength for the level estimation model with respect to the reference blood component.

According to an exemplary embodiment, a material having an interrelationship with the target blood component may be used as the reference blood component. Here, the term 'having an interrelationship' refers to a characteristic in which level changes or concentration changes of two components included in blood have a certain relationship therebetween within a specific time range. For example, a linear proportional relation or linearly inversely proportional relation is made between levels of two materials having an interrelationship or function relationship having a secondary function or more may be made therebetween. The controller 140 may estimate a more accurate level of the target blood component using the interrelationship between the target blood component and the reference blood component.

Types of materials used for the target blood component and the reference blood component have no specific limitation as long as having an interrelationship therebetween. Further, it is unnecessary that only one material may be certainly used for the reference blood component, and multiple blood components may be used for the reference blood component. As the number of the reference blood components having an interrelationship with the target blood component is increased, it is clear that the accuracy of the target blood component level estimated by the controller 140 is increased.

For examples of two blood components having an interrelationship with each other, there are a neutral fat and sugar. When a person generally eats food, more specifically, carbohydrates, the carbohydrates are converted into blood sugar in his or her body, and thus, a blood sugar level is increased instantaneously. Further, when the blood sugar level is increased, insulin, which is a peptide hormone for decomposing blood sugar, is secreted from a pancreas to decompose the blood sugar, and thus the blood sugar level is decreased. The decomposed blood sugar is used for an energy source, and when an amount of the eaten carbohydrate is greater than an amount of necessary energy or energy to be used, insulin converts excessive blood sugar into neutral fats for adjustment of blood sugar. As a result, an amount of neutral fats is increased, and thus, an inversely proportional relationship in which the blood sugar level is decreased in a section in which a neutral fat level is increased in blood occurs.

The controller 140 generally utilizes a predetermined level estimation model for estimating the target blood component level. Here, the level estimation model includes an algorithm for estimating the target blood component level. As described above, since the controller 140 estimates the target blood component level using the spectrum data for each wavelength extracted by the detector 130 together with the reference blood component level, the spectrum data for each wavelength and the reference blood component level become an input parameter of such a level estimation model. That is, the level estimation model of the controller 140 used for estimating the target blood component level may be expressed by a combination of a wavelength function whose parameter is the spectrum data for each wavelength and a reference function whose parameter is the reference blood component level.

FIG. 2 is an example of a level estimation model used for the controller 140 conceptually expressed by using an equation. In FIG. 2, $Y_T$ denotes an estimated value with respect to a target blood component, $y_R$ denotes a reference blood component level, and $w_1$, $w_2$, and $w_n$ denote n (n is an integer greater than or equal to 2) pieces of spectrum data for each wavelength. Referring to FIG. 2, it is shown that the level estimation model may be defined by a predetermined function whose input parameter is each of the spectrum data for each wavelength and the reference blood component level, that is, a combination function F of a wavelength function $f_1$ and a reference function $f_2$. Further, in FIG. 2, the combination function F is expressed by the sum of the wavelength function $f_1$ and the reference function $f_2$, and this is merely an example with respect to the combination of the wavelength function $f_1$ and the reference function $f_2$. It is clear that the combination function F can be expressed by the sum of the wavelength function $f_1$ and the reference function $f_2$, and also by multiplication or another mathematic relationship.

Further, the combination function F which defines the level estimation model may be derived by using a group of measured values which are sample data. For example, the combination function F may be derived by using a measured value of a spectrum for each wavelength, a measured value of a target blood component, and a measured value of a reference blood component. Here, the term 'for each wavelength spectrum measured value' may be spectrum data for each wavelength obtained from a spectrum of reflected light extracted by a detector after actual measurement is performed at a specific point. Further, the term 'a measured value of a target blood component' and the term 'a measured value of a blood sample component' respectively refer to a measured value of the target blood component and a measured value of the reference blood component at each corresponding measured point, that is, each point when the measured value of the spectrum for each wavelength is obtained.

According to one aspect, the term 'the measured value of the target blood component' and 'the measured value of the reference blood component' used for deriving the combination function F may refer to, for example, actual measured levels of the target blood component or the reference blood component using a blood sample prepared at each measurement point, but are not limited thereto. For example, at least one of the terms 'the measured value of the target blood component' and 'the measured value of the reference blood component' may be a value obtained on the basis of a known interrelation between the target blood component and the reference blood component based on a specific situation in which time has elapsed after food had been taken in, after exercise had been performed, or the like, or a value estimated using a different level estimation model from the level estimation model used in the exemplary embodiment.

FIG. 3 shows equations for describing a process of deriving a combination function F using a measured value of a spectrum for each wavelength, a measured value of a target blood component, and a measured value of a reference blood component. In FIG. 3, $t_1$ to $t_m$ (m is an integer greater than or equal to 2) each refer to a time when actual measurement is performed, and may refer to times measured with a predetermined time interval (e.g., 30 minutes), for example, after food had been taken in or exercise had been performed. Further, $w_{11}$ to $w_{n1}$ refer to measured values of a spectrum for each wavelength at time $t_1$, $w_{12}$ to $w_{n2}$ refer to measured values of a spectrum for each wavelength at time $t_2$, $w_{1m}$ to $w_{nm}$ refer to measured values of a spectrum for each wavelength at time $t_m$, $Y'_{T1}$ to $Y'_{Tm}$ respectively refer to measured values of a target blood component $Y_T$ at times $t_1$ to $t_m$, and $y'_{R1}$ to $y'_{Rm}$ respectively refer to measured values of a reference blood component ($y_R$) at times $t_1$ to $t_m$. Referring to FIG. 3, when m equations are solved with the measured values of the spectrum for each wavelength, the measured values of the target blood component, and the measured values of the reference blood component, it is clear that the combination function F can be derived.

As described above, in the apparatus for estimating a blood component level 100, the controller 140 estimates the target blood component level using the spectrum data for each wavelength extracted by the spectrometer 130 together with the reference blood component level corresponding to spectrum data. That is, in the level estimation model of the controller 140 used for estimating the target blood component level, the reference blood component level is also a factor, that is, serves as an input parameter, in addition to the spectrum data for each wavelength. Further, when the reference blood component level is used for the level estimation model as an additional input parameter, a difference between the estimated value of the target blood component and the measured value is reduced, and thereby a correlation coefficient is increased. Here, the term 'correlation coefficient' refers to a ratio of the estimated value to the measured value.

Table 1 shows an example of a correlation coefficient with respect to a blood neutral fat level. In Table 1, a correlation coefficient estimated using spectrum data for each wavelength according to a related-art method and correlation coefficient estimated using spectrum data for each wavelength and a blood sugar level corresponding to the spectrum data as a reference blood component according to the above-described exemplary embodiment are each disclosed. In Table 1, JSDU refers to a product name as Micro NIR Pro Spectrometer made by the JDSU Uniphase Corporation, and FTIR refers to a Fourier transform NIR spectrometer. Further, the subscripts 'in' and 'out' respectively refer to an inner side and an outer side of a wrist as measuring portions. Referring to Table 1, it shows that the correlation coefficient according to the exemplary embodiment is improved at least about 20% and maximally about 400% or greater when compared to the method in the related art.

TABLE 1

| Input parameter | Correlation coefficient | | | |
|---|---|---|---|---|
| | JDSU_in | JDSU_out | FTIR_in | FTIR_out |
| Spectrum | 0.1742 | 0.3371 | 0.5241 | 0.1499 |
| Spectrum & blood sugar | 0.6508 | 0.7180 | 0.6631 | 0.6155 |

Table 2 shows an example of a correlation coefficient with respect to a blood sugar level. In Table 2, a correlation coefficient estimated using only spectrum data of for each wavelength according to a method in the related art, and a correlation coefficient estimated using spectrum data for each wavelength together with a blood neutral fat level corresponding to the spectrum data as a reference blood component according to the above-described exemplary embodiment are respectively disclosed. In Table 2, JSDU also refers to a product name as Micro NIR Pro Spectrometer made by the JDSU Uniphase Corporation, and FTIR also refers to a Fourier transform NIR spectrometer. Further, the subscripts 'in' and 'out' respectively refer to an inner side and an outer side of a wrist as measuring portions. Referring to Table 2, it shows that the correlation coefficient according to the exemplary embodiment is improved at least about 50% and maximally about 300% or greater when compared to the method in the related art.

TABLE 2

| Input parameter | Correlation coefficient | | | |
|---|---|---|---|---|
| | JDSU_in | JDSU_out | FTIR_in | FTIR_out |
| Spectrum | 0.4616 | 0.1865 | 0.3986 | 0.4333 |
| Spectrum & blood neutral fat | 0.7886 | 0.6481 | 0.6481 | 0.6992 |

Figure 4A:
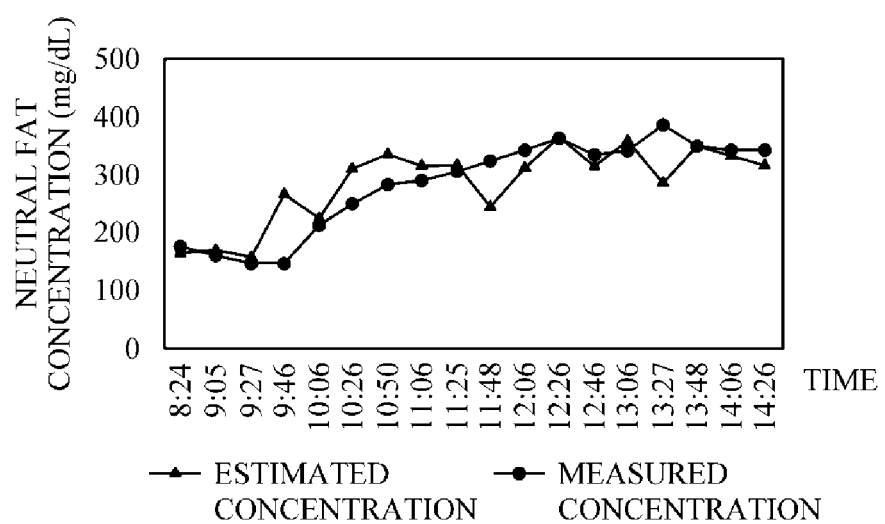
FIG. 4A is a graph illustrating concentration changes of blood neutral fat over time.
Figure 4B:
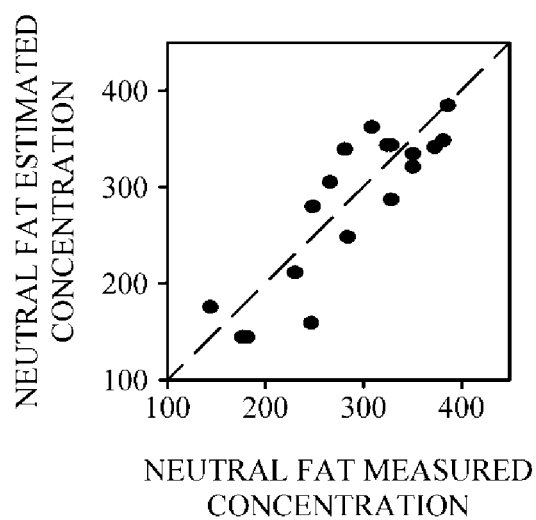
FIG. 4B is a graph illustrating a correlation coefficient of concentration of blood neutral fat at each of the points used for measurements shown in FIG. 4A.

FIG. 4A is a graph illustrating concentration changes of blood neutral fat over time, and FIG. 4B is a graph illustrating a correlation coefficient of the concentration of blood neutral fat at each of the points used for measurements shown in FIG. 4A. In FIGS. 4A and 4B, each measured concentration refers to a concentration of neutral fats actually measured after a blood sample is extracted, and an estimated concentration refers to a concentration of neutral fats estimated according to the above-described exemplary embodiment. Referring to FIG. 4A, although a difference of a predetermined size between the measured concentration and the estimated concentration exists at some points, generally, it shows that values of the two concentrations are similar to each other in spite of elapsed time. Similar to the above, referring to FIG. 4B, it shows that the correlation coefficient of the concentration of neutral fats is close to a straight line having a slope of 45 degrees, that is, the correlation coefficient is close to 1.

Figure 5:
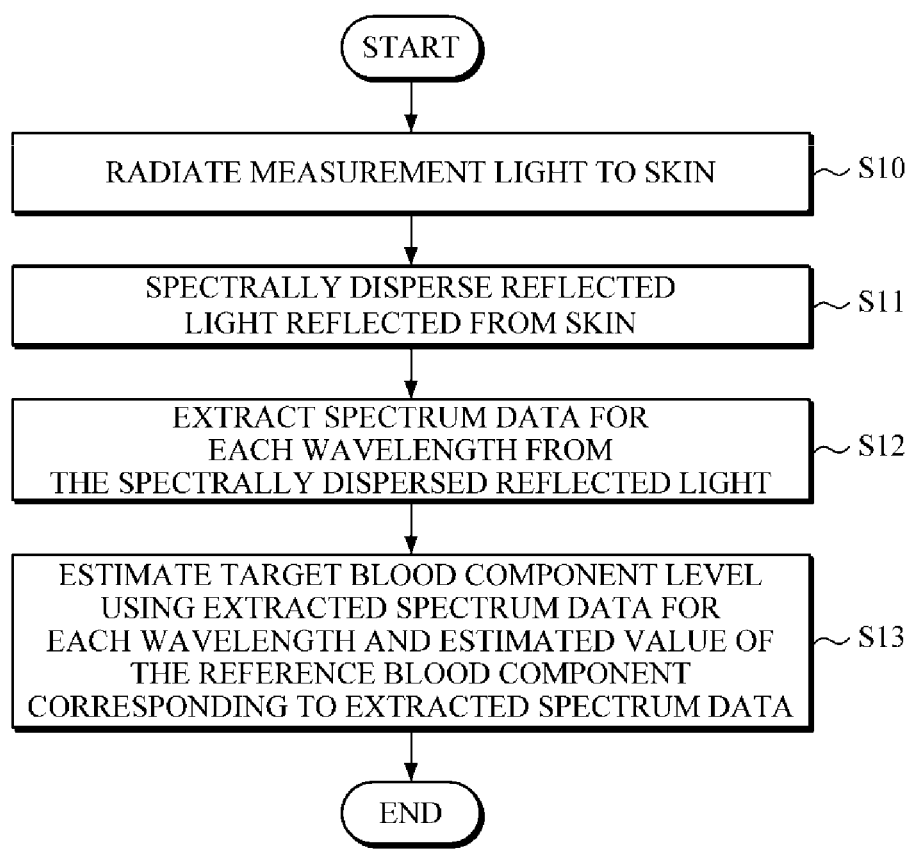
FIG. 5 is a flowchart for describing an example of a procedure of estimating a predetermined blood component using the apparatus for estimating a blood component level shown in FIG. 1.

Next, a procedure for estimating a predetermined blood component using the apparatus for estimating a blood component level 100 shown in FIG. 1 will be described. FIG. 5 is a flowchart illustrating an example of such an estimate procedure, and the estimate procedure will be briefly described below. Therefore, the above descriptions described with reference to FIGS. 1 to 3 may be applied to descriptions not to be specifically described herein.

Referring to FIGS. 1 and 5, the light source 110 emits predetermined measurement light to skin, which is a target to be measured by the apparatus 100 (operation S10). Further, the emitted light is reflected from the skin and spectrally dispersed by the spectrometer 120 of the apparatus 100 (operation 511). That is, the spectrometer 120 receives the reflected light from the skin and decomposes the reflected light on the basis of a difference of a wavelength. Subsequently, the detector 130 extracts spectrum data for each wavelength from the spectrally dispersed reflected light (operation S12). Finally, the controller 140 applies the extracted spectrum data for each wavelength and the estimated value of the reference blood component corresponding to the extracted spectrum data to a preset level estimation model so as to estimate a target blood component level (operation S13).

While not restricted thereto, the operations or steps of the methods or algorithms according to the above exemplary embodiments may be embodied as computer-readable codes on a computer-readable recording medium. The computer-readable recording medium may be any recording apparatus capable of storing data that is read by a computer system. Examples of the computer-readable recording medium include read-only memories (ROMs), random-access memories (RAMs), CD-ROMs, magnetic tapes, floppy disks, and optical data storage devices. The computer-readable recording medium may be a carrier wave that transmits data via the Internet, for example. The computer-readable medium may be distributed among computer systems that are interconnected through a network so that the computer-readable code is stored and executed in a distributed fashion. Also, the operations or steps of the methods or algorithms according to the above exemplary embodiments may be written as a computer program transmitted over a computer-readable transmission medium, such as a carrier wave, and received and implemented in general-use or special-purpose digital computers that execute the programs. Moreover, it is understood that in exemplary embodiments, one or more units (e.g., detector 130 and controller 140 illustrated in FIG. 2) of the above-described apparatuses and devices can include or implemented by circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating a blood component level, the apparatus comprising:
a light source configured to emit a light toward a skin;
a spectrometer configured to spectrally disperse the light reflected from the skin;
a detector configured to detect a spectrum of the spectrally dispersed light to extract spectrum data for each wavelength; and
a processor configured to estimate a blood neutral fat level based on a blood neutral fat estimation model that uses the extracted spectrum data as a sole parameter, and estimate a blood sugar level by applying the extracted spectrum data and the blood neutral fat level corresponding to the spectrum data to a blood sugar level estimation model that uses an inverse proportional relation between the blood neutral fat level and the blood sugar level.

2. The apparatus of claim 1, wherein the blood sugar level estimation model is derived from an amount of the extracted spectrum data, a plurality of measured values of the blood sugar, and a plurality of measured values of the blood neutral fat which respectively correspond to the amount of the extracted spectrum data.

3. The apparatus of claim 2, wherein the detector is further configured to extract the amount of the spectrum data at a constant time interval.

4. The apparatus of claim 2, wherein each of the plurality of measured values of the blood sugar and the plurality of measured values of the blood neutral fat is measured directly from a blood sample.

5. An apparatus for estimating a blood neutral fat level, the apparatus comprising:
a light source configured to emit a light toward a skin;
a spectrometer configured to spectrally disperse the light reflected from the skin;
a detector configured to detect a spectrum of the spectrally dispersed light to extract spectrum data for each wavelength; and
a processor configured to apply the extracted spectrum data and a blood sugar level corresponding to the spectrum data to a blood neutral fat level estimation model that uses an inverse proportional relation between the blood neutral fat level and a blood sugar level, to estimate the blood neutral fat level.

6. The apparatus of claim 5, wherein the blood neutral fat level model uses an algorithm which is a combination of a wavelength function and a reference function representing the inverse proportional relation between the blood neutral fat level and the blood sugar level, and
wherein the wavelength function has the extracted spectrum data as a parameter, and the reference function has the blood sugar level as a parameter.

7. The apparatus of claim 6, wherein the blood neutral fat level estimation model is derived from an amount of the extracted spectrum data, a plurality of measured values of blood neutral fat, and a plurality of measured values of blood sugar which respectively correspond to the amount of the extracted spectrum data.

8. The apparatus of claim 7, wherein the detector is further configured to extract the amount of the spectrum data at a constant time interval.

9. The apparatus of claim 7, wherein each of the plurality of measured values of blood neutral fat and the plurality of measured values of blood sugar is measured directly from a blood sample.

10. The apparatus of claim 6, wherein the reference function is a function determined based on an interrelation between the blood neutral fat and the blood sugar.

11. The apparatus of claim 5, wherein the blood neutral fat level is estimated by applying the extracted spectrum data to a second level estimation model of the processor for estimating the blood sugar level.

12. The apparatus of claim 11, wherein the second level estimation model uses an algorithm expressed by a function having the extracted spectrum data as a sole parameter.

13. An apparatus for estimating a blood sugar level, the apparatus comprising:
a light source configured to emit a light toward a skin;
a spectrometer configured to spectrally disperse the light reflected from the skin;
a detector configured to detect a spectrum of the spectrally reflected light to extract spectrum data for each wavelength; and
a processor configured to estimate the blood sugar level by applying the extracted spectrum data and a blood neutral fat level corresponding to the spectrum data to a blood sugar level estimation model that uses an inverse proportional relation between the blood neutral fat level and the blood sugar level.

14. The apparatus of claim 13, wherein:
the blood neutral fat level is estimated by applying the extracted spectrum data to a blood neutral fat level estimation model
that is expressed by a function having the extracted spectrum data as a sole parameter.

* * * * *